United States Patent

Merger et al.

[11] 4,324,727
[45] Apr. 13, 1982

[54] PREPARATION OF BUTYROLACTONES

[75] Inventors: Franz Merger, Frankenthal; Gerhard Nestler, Ludwigshafen, both of Fed. Rep. of Germany

[73] Assignee: BASF Aktiengesellschaft, Ludwigshafen, Fed. Rep. of Germany

[21] Appl. No.: 238,980

[22] Filed: Feb. 27, 1981

[30] Foreign Application Priority Data

Mar. 13, 1980 [DE] Fed. Rep. of Germany ....... 3009604

[51] Int. Cl.³ .......................................... C07D 307/32
[52] U.S. Cl. .................................................. 260/343.6
[58] Field of Search ..................................... 260/343.6

[56] References Cited

U.S. PATENT DOCUMENTS

| | | | |
|---|---|---|---|
| 2,986,568 | 3/1961 | Johnston | 260/343.6 |
| 3,299,100 | 1/1967 | Phillips | 260/343.6 |
| 3,952,020 | 4/1976 | Stapp | 260/343.6 |
| 3,957,827 | 10/1974 | Lyons | 260/343.6 |
| 3,963,757 | 6/1976 | Stapp | 260/343.6 |
| 4,031,114 | 6/1977 | Kurkov | 260/343.6 |
| 4,031,115 | 6/1977 | Kurkov | 260/343.6 |

FOREIGN PATENT DOCUMENTS 1192178  5/1965  Fed. Rep. of Germany .

OTHER PUBLICATIONS

Houben–Weyl, "Methoden der Organischen Chemie" Band VI/2 (1963), pp. 571–580.

Primary Examiner—Henry R. Jiles
Assistant Examiner—Jane T. Fan
Attorney, Agent, or Firm—John H. Shurtleff

[57] ABSTRACT

A process for the preparation of a butyrolactone of the general formula

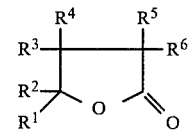

where $R^1$ is unsubstituted or substituted alkyl or phenyl and $R^2$ to $R^6$ are hydrogen or unsubstituted or substituted alkyl or phenyl, wherein a γ-formylcarboxylic acid ester of the formula

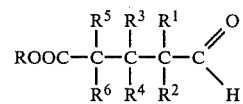

where R is lower alkyl, is treated with oxygen at an elevated temperature of 60°–150° C.

2 Claims, No Drawings

PREPARATION OF BUTYROLACTONES

The present invention relates to a process for the preparation of butyrolactones by reacting γ-formylcarboxylic acid esters with oxygen at an elevated temperature.

Butyrolactones are valuable and versatile intermediates which are used, for example, in the preparation of herbicides and drugs (cf., for example, German Laid-Open Applications Nos. DOS 2,715,284 and 2,715,133).

Butyrolactones can be prepared, for example, by intramolecular cyclization of γ-hydroxycarboxylic acids or γ-halocarboxylic acids or of their derivatives. This method of synthesis, described in Houben-Weyl, "Methoden der Organischen Chemie", 1963, volume 6/2, pages 571–580, has, because of difficulties in the preparation of the requisite starting materials, only achieved industrial importance in a few special cases.

In addition, butyrolactones may be prepared, for example, by reacting a malonic acid ester with an epoxide in the presence of an alkali metal alcoholate (U.S. Pat. No. 3,299,100); by reducing a 1,2-dicarboxylic acid anhydride in the presence of a special ruthenium catalyst (U.S. Pat. No. 3,957,827); by reacting bromoacetic acid or an acid derivative thereof with an α-olefin at an elevated temperature in the presence of a source of free radicals (U.S. Pat. No. 2,986,568); by treating a γ-haloalcohol with hydrocyanic acid or with a cyanide in the presence of a phosphine (U.S. Pat. No. 3,963,757); by reaction of an α-monobranched aliphatic aldehyde with carbon monoxide in the presence of an acidic catalyst (German Pat. No. 1,192,178); or by reaction of a β-olefin with formaldehyde or acetaldehyde and carbon monoxide in the presence of rhodium chloride under high pressure and at a high temperature (U.S. Pat. No. 3,952,020).

These conventional processes have the disadvantage that they start from compounds which are expensive and difficult to obtain (U.S. Pat. Nos. 3,299,100, 3,957,827 and 2,986,568) or that, because of the use of a toxic starting material, such as hydrocyanic acid, a cyanide or carbon monoxide, they require an expensive technology (U.S. Pat. Nos. 3,963,757 and 3,952,020, and German Pat. No. 1,192,178). Drastic conditions, such as high pressure and high temperatures, in many cases complicate the industrial implementation of the process and rule out the use of starting materials with valuable substituents, such as cyanide groups and carboxyl groups. The processes furthermore in some cases give mixtures of isomeric products, which are very difficult to separate.

We have found, surprisingly, that butyrolactones of the general formula

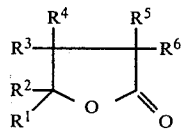

where $R^1$ is unsubstituted or substituted alkyl or phenyl and $R^2$ to $R^6$ are hydrogen or unsubstituted or substituted alkyl or phenyl may be prepared particularly advantageously by treating a γ-formylcarboxylic acid ester of the general formula

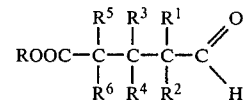

where R is lower alkyl, with oxygen at an elevated temperature.

Using the novel process, the butyrolactones are obtained smoothly and in good yield. This result is very surprising, since it is generally known that the oxidation of aldehydes with oxygen in the main gives the corresponding carboxylic acids or anhydrides (Houben-Weyl, Methoden der Organischen Chemie, 1952, volume 8, page 24).

In the γ-formylcarboxylic acid esters of the formula II, the alkyl and phenyl groups $R^1$ to $R^6$ may contain one or more substituents which are inert under the reaction conditions, such as cyano, alkoxycarbonyl, alkylcarbonyloxy, nitro or chlorine. Alkyl $R^1$ to $R^6$ is, for example, of 1 to 8, preferably of 1 to 6, carbon atoms. Lower alkyl R is, for example, alkyl of up to 4 carbon atoms. Particularly preferred γ-formylcarboxylic acid esters of the formula II are those where R is methyl, ethyl, propyl or butyl, $R^1$ and $R^2$ are alkyl of 1 to 6 carbon atoms, which may be substituted, for example by cyano, methoxycarbonyl, acetoxy, nitro, phenyl or chlorine, and $R^3$ to $R^6$ are hydrogen.

Examples of starting materials are methyl or ethyl 4-formyl-4-methyl-valerate, methyl or ethyl 4-formyl-4-ethyl-valerate, methyl or ethyl 4-formyl-4-propyl-valerate, methyl or ethyl 4-formyl-4-butyl-valerate, methyl 4-formyl-4-ethyl-hexanoate, methyl 4-formyl-4-ethyl-heptanoate, methyl 4-formyl-4-propyl-hexanoate, methyl or ethyl 4-formyl-3,4-dimethyl-valerate, methyl 4-formyl-2,4-dimethyl-valerate, methyl 4-formyl-4-(β-cyanoethyl)-hexanoate and methyl 4-formyl-4-(β-methoxycarbonylethyl)-hexanoate.

In contrast to the conventional processes, the process according to the invention is extremely simple to carry out industrially. The starting materials are easily obtainable. For example, the requisite γ-formylcarboxylic acid esters can be prepared by conventional processes from the corresponding aldehydes or enamines and α,β-unsaturated esters (Organic Reactions, Vol. 10, page 179).

The novel process is in general carried out by passing oxygen into the γ-formylcarboxylic acid ester, advantageously whilst stirring at 60°–150° C. Either technical-grade oxygen or air or some other oxygen/inert gas mixture can be used. The gas is advantageously introduced at 5–50 l/hour and the total amount of oxygen introduced is advantageously 2–10 moles/mole of formylcarboxylic acid ester. The reaction is complete after about 2–10 hours. Advantageously, it is carried out in the absence of a solvent, but can also be carried out in the presence of an inert solvent, for example benzene, chlorobenzene or nitromethane.

In general, the reaction is carried out without a catalyst. In order to achieve higher reaction rates and better selectivities, it may however at times be advantageous to use a catalyst. Examples of suitable catalysts are heavy metal salts, such as $NiCl_2$, $Ni(OAc)_2$, $VCl_3$, $CrCl_3$, $CoCl_2$ or $CeCl_3$. The amount of catalyst is not critical and is in general from 0.01 to 0.1 mole percent, based on starting material. Whether a catalyst is required at all, and what catalyst is advantageous, can in each case be established easily by a preliminary experiment.

The reaction can be carried out under atmospheric or superatmospheric pressure. The reaction mixture is worked up by conventional methods, such as distillation.

EXAMPLE 1

316 parts of methyl 4-formyl-4-methyl-valerate are heated to 100° C. in a stirred reactor and 150 parts of oxygen (120 liters) are then introduced into the stirred material through a sintered glass frit, in the course of 4 hours. After completion of the reaction, the mixture is subjected to fractional distillation. 180 parts (79% of theory) of γ,γ-dimethyl-γ-butyrolactone (boiling point 80°–82° C./16 mbar) are obtained.

EXAMPLE 2

Using a method similar to Example 1, 186 parts of methyl 4-formyl-4-methyl-heptanoate are reacted with 80 parts of oxygen in the course of 5 hours. 86 parts (61% of theory) of γ-methyl-γ-propyl-γ-butyrolactone (boiling point 117°–119° C./20 mbar) are obtained.

EXAMPLE 3

Using a method similar to Example 1, 172 parts of methyl 4-formyl-3,4-dimethyl-valerate are reacted with 80 parts of oxygen in the course of 4 hours. 91 parts (71% of theory) of β,γ,γ-trimethyl-γ-butyrolactone (boiling point 94°–96° C./16 mbar) are obtained.

EXAMPLE 4

Using a method similar to Example 1, a mixture of 244 parts of methyl 4-formyl-4-(β-methoxycarbonylethyl)-hexanoate and 2.4 parts of $CoCl_2 \cdot 6H_2O$ is reacted with 100 parts of oxygen in the course of 5 hours. The batch is then washed with water, dried with anhydrous magnesium sulfate and subjected to fractional distillation. 113 parts (56% of theory) of γ-ethyl-γ-(β′-methoxycarbonylethyl)-γ-butyrolactone (boiling point 125° C./0.5 mbar) are obtained.

We claim:

1. A process for the preparation of a butyrolactone of the formula

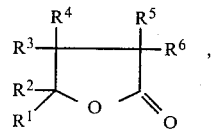

where $R^1$ is unsubstituted or substituted alkyl or phenyl and $R^2$ to $R^6$ are hydrogen or unsubstituted or substituted alkyl or phenyl, which comprises:

treating a γ-formylcarboxylic acid ester of the formula

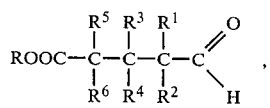

where R is lower alkyl, with oxygen at an elevated temperature of 60°–150° C.

2. A process as claimed in claim 1, wherein, in the γ-formylcarboxylic acid ester of the formula II, R is methyl, ethyl, propyl or butyl, $R^1$ and $R^2$ are alkyl of 1 to 6 carbon atoms, which may be substituted by cyano, acetoxy, methoxycarbonyl, phenyl, nitro or chlorine, and $R^3$ to $R^6$ are hydrogen.

* * * * *